United States Patent [19]

Niikura et al.

[11] Patent Number: 5,254,594
[45] Date of Patent: Oct. 19, 1993

[54] REMEDIES FOR BONE DISEASES

[75] Inventors: Kazuaki Niikura; Yoshimitsu Nakajima; Yoshitada Notsu; Ryuji Ono; Osamu Nakayama, all of Ibaraki, Japan

[73] Assignee: Klinge Pharma GmbH, Munich, Fed. Rep. of Germany

[21] Appl. No.: 865,106

[22] Filed: Apr. 8, 1992

[30] Foreign Application Priority Data

Apr. 9, 1991 [JP] Japan .................. 3-166944

[51] Int. Cl.⁵ .......................... A61K 31/135
[52] U.S. Cl. .................. 514/648; 514/651; 514/874
[58] Field of Search ............ 514/648, 651, 874

[56] References Cited

U.S. PATENT DOCUMENTS

| | | | |
|---|---|---|---|
| 4,206,234 | 6/1980 | Richardson | 424/330 |
| 4,623,660 | 11/1986 | Richardson | 514/514 |
| 4,729,999 | 3/1988 | Young | 514/227 |
| 4,894,373 | 1/1990 | Young | 514/239.2 |
| 5,047,431 | 9/1991 | Schickaneder et al. | 514/648 |

FOREIGN PATENT DOCUMENTS 0054168 10/1981 European Pat. Off.

OTHER PUBLICATIONS

Hulka, B. S. "Replacement Estrogens and Risk of Gynecologic Cancers and Breast Cancer", Estrogens and Cancer, 60:1960-1964 (Oct. 1987).

Primary Examiner—Frederick E. Waddell
Assistant Examiner—Minna Moezie
Attorney, Agent, or Firm—Brumbaugh Graves Donohue & Raymond

[57] ABSTRACT

Remedies for bone diseases comprising, as active ingredient, droloxifene or a salt thereof.

3 Claims, No Drawings

REMEDIES FOR BONE DISEASES

FIELD OF THE INVENTION

This invention relates to remedies for bone diseases comprising, as active ingredient, droloxifene having the chemical structure represented by the following formula,

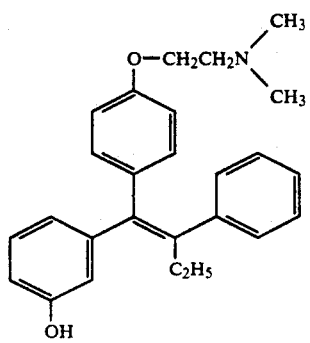

or a salt thereof approved as a drug, which are to be used in the field of medical treatment.

PRIOR ART

Droloxifene is a known compound disclosed in Japanese Patent Publication No. 39347/1985 and European Patent 0 054 168, in which it is described that this compound is useful as an anti-tumor agent, particularly as a remedy for tumors of the breast.

However, it is not known that droloxifene is also useful for the relief of bone diseases caused by the deficiency of estrogen or the like, which are often observed in women after menopause or those with the ovarium being excised.

On the other hand, it was disclosed in Japanese Patent Kokai No. 178917/1986 that tamoxifen and clomiphene, both having a chemical structure similar to that of droloxifene, are useful for the relief of osteoporosis.

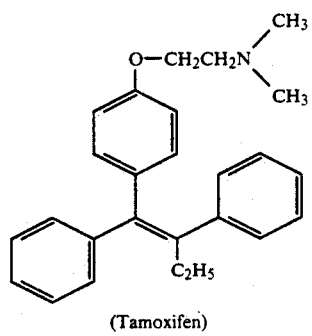

(Tamoxifen)

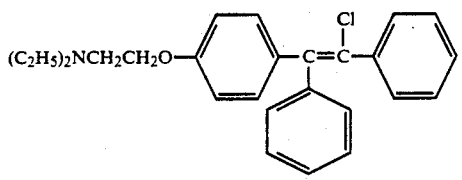

(Clomiphene)

PROBLEMS TO BE SOLVED BY THE INVENTION

Though useful as a remedy for osteoporosis, tamoxifen and clomiphene are known to have a side effect of increasing the uterine weight.

It is quite presumable that the increase in the uterine weight will be related to the growth of uterine cancers, because of the facts that administration of estrogen, which is a remedy for osteoporosis, is liable to cause uterine cancers [Cancer, 60, 1960-1964 (1987)], and that its administration also causes a marked increase in the uterine weight.

MEANS TO SOLVE THE PROBLEMS

This invention was accomplished under the circumstances described above, and provides remedies for bone diseases having lower side effects, such as the increase in the uterine weight.

The remedies for bone diseases of this invention comprise, as active ingredient, droloxifene or a salt thereof approved as a drug.

The salts of droloxifene approved as drugs are salts of non-toxic type commonly used, such as salts with organic acids (e.g., formic, acetic, trifluoroacetic, citric, maleic, tartaric, methanesulfonic, benzenesulfonic and toluenesulfonic acids), inorganic acids (e.g., hydrochloric, hydrobromic, sulfuric and phosphoric acids), and amino acids (e.g., aspartic and clutamic acids). These salts may be prepared by the methods commonly employed.

The remedies for bone diseases of this invention may be administered to animals including humans orally or parenterally in the conventional form of preparations, such as capsules, microcapsules, tablets, granules, powder, troches, pills, suppositories, injections, suspensions and syrups.

The remedies for bone diseases of this invention can be prepared by the methods commonly employed using conventional, organic or inorganic additives, such as an excipient (e.g., sucrose, starch, mannitol, sorbitol, lactose, glucose, cellulose, talc, calcium phosphate and calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose and starch), a disintegrator (e.g., starch, carboxymethylcellulose, hydroxypropylstarch, low substituted hydroxypropylcellulose, sodium bicarbonate, calcium phosphate and calcium citrate), a lubricant (e.g., magnesium stearate, light anhydrous silicic acid, talc and sodium lauryl sulfate), a flavoring agent (e.g., citric acid, menthol, glycine and orange powder), a preservative (e.g., sodium benzoate, sodium bisulfite, methylparaben and propylparaben), a stabilizer (e.g. citric acid, sodium citrate and acetic acid), a suspending agent (e.g., methylcellulose, polyvinylpyrrolidone and alminum stearate), a dispersing agent (e.g., hydroxypropylmethylcellulose), a diluent (e.g., water), and base wax (e.g., cocoa butter, white petrolatum and polyethylene glycol). The amount of the active ingredient in the medical composition may be at a level that will exercise the desired therapeutical effect; for example, about 1 mg to 100 mg in unit dosage for both oral and parenteral administration.

The active ingredient may be usually administered once to four times a day with a unit dosage of 0.25 mg to 100 mg, but the above dosage may be properly varied depending on the age, body weight and illness conditions of the patients and on the type of administration.

EFFECTS ACHIEVED BY THE INVENTION

Described below is the result of a pharmacological test on droloxifene which is an active ingredient of the remedies for bone diseases of this invention.

Compounds Tested (1) Droloxifene (citrate)
(2) Tamoxifen(citrate)
(3) Clomiphene (hydrochloride)
(4) 17β-Estradiol

Test Method

The ovaria on both sides are collected from each of the test animals (female, Wister rats 10 weeks old) under a general anesthetic, a test compound in the form of 0.5% suspension in methylcellulose is orally administered on the next day in an amount of 5 ml/Kg, and this administration is continued over a period of four weeks once a day except Saturdays and Sundays. Fasting is then started in the evening, and the right femurs and the uterus are collected on the next day. These femurs are heated at 110° C. for six hours, and its length is measured. In addition, its width and the amount of salts contained are measured at the position of 18/100 from its distal end by using single photon absorptiometer and the bone density is calculated according to the following formula. The uterine weight is measured at sacrifice, and is divided by the body weight. The recovery rate of bone density and the rate of increase in the uterine weight are calculated by letting the difference in data between the control group and the group to which no test compound is administered be 100%.

$$\text{Bone Density} = \frac{\text{Amount of Salts}}{(\text{Bone Width})^2}$$

Test Result

TABLE 1

| Test Compound | Dosage | Recovery Rate of Bone Density (%) | Rate of Increase in Uterine Weight (%) |
|---|---|---|---|
| 1 | 3.2 mg/Kg | 51 | 26 |
|   | 10 mg/Kg | 72 | 29 |
|   | 32 mg/Kg | 84 | 32 |
| 2 | 1 mg/Kg | 70 | 40 |
|   | 3.2 mg/Kg | 93 | 42 |
| 3 | 3.2 mg/Kg | 62 | 43 |
|   | 10 mg/Kg | 113 | 51 |
| 4 | 1 mg/Kg | 91 | 98 |

TABLE 1-continued

As may be seen from the test result shown above, droloxifene has an action of recovering bone density, and is therefore useful as a remedy for bone diseases characterized by abnormalities of bone metabolism, such as osteoporosis, Paget's bone diseases, bone dissolution, malignant hypercalcemia, and chronic articular rheumatism.

Furthermore, droloxifene has lower side effect of increasing the uterine weight compared with conventional remedies for bone diseases, such as tamoxifen, clomiphene and 17β-estradiol.

The following example will further illustrate the invention.

EXAMPLE 1

| | |
|---|---|
| Droloxifene citrate | 100 g |
| Lactose | 1190 g |
| low substituted hydroxypropylcellulose | 250 g |
| Polyvinylpyrrolidone | 50 g |
| Magnesium stearate | 10 g |

The components listed above were mixed together by the usual method, and the mixture thus obtained was compressed into 10,000 tablets each containing 10 mg of droloxifene citrate.

These tablets were then subjected to film coating by the usual method, thus giving film-coated tablets.

We claim:

1. A method of treating bone diseases characterized by abnormalities in bone metabolism comprising administering to a patient suffering from bone disease a therapeutically effective amount of droloxifene or a pharmaceutically acceptable salt thereof.

2. A method according to claim 1, wherein droloxifene is administered in an amount of from 1 mg to 100 mg per day.

3. A method according to claim 1, wherein the bone disease is selected from the group consisting of osteoporosis, Paget's bone disease, bone dissolution, malignant hypercalcemia and chronic articular rheumatism.

* * * * *